(12) United States Patent
Dharmapuri Murali et al.

(10) Patent No.: US 12,232,881 B1
(45) Date of Patent: Feb. 25, 2025

(54) METHOD AND SYSTEM TO ASSESS WHETHER ELECTRICAL RECORDINGS DURING CARDIAC MAPPING LIE ON THE MYOCARDIAL SURFACE

(71) Applicant: Neucures Inc., Los Angeles, CA (US)

(72) Inventors: Vijay Raghavan Dharmapuri Murali, Bengaluru (IN); Kappagantula Gopalakrishna Murty, Nanaimo (CA); Rohit Jain, Danville, CA (US)

(73) Assignee: Anumana, Inc., Cambridge, MA (US)

( * ) Notice: Subject to any disclaimer, the term of this patent is extended or adjusted under 35 U.S.C. 154(b) by 859 days.

(21) Appl. No.: 17/340,002

(22) Filed: Jun. 5, 2021

(51) Int. Cl.
*A61B 5/367* (2021.01)
*A61B 5/00* (2006.01)

(52) U.S. Cl.
CPC ............ *A61B 5/367* (2021.01); *A61B 5/6852* (2013.01); *A61B 5/6869* (2013.01)

(58) Field of Classification Search
CPC ...... A61B 5/367; A61B 5/6852; A61B 5/6869
See application file for complete search history.

(56) References Cited

U.S. PATENT DOCUMENTS

2019/0069954 A1\* 3/2019 Cohen .................... A61B 6/503

\* cited by examiner

Primary Examiner — Joseph M Dietrich
(74) Attorney, Agent, or Firm — Caldwell Intellectual Property Law (57) ABSTRACT

According to one embodiment, a method for generating a cardiac map is disclosed. The method comprises during cardiac mapping in which a mapping catheter is inserted into a heart, receiving a plurality of recordings from the mapping catheter, each recording includes a voltage, and the spatial coordinates of a recording site within the heart indicative of an electrode position of the mapping catheter at the time of acquisition of said voltage, constructing a three-dimensional surface of the heart based on the spatial coordinates of each recording site, performing surface analysis to determine off-surface points in the plurality of recordings where each off-surface point corresponds to a recording from the plurality of recordings which does not lie on the three-dimensional surface, and selectively moving at least some of the off-surface points to the three-dimensional surface based on a predefined threshold.

13 Claims, 13 Drawing Sheets

---

RECEIVE A PLURALITY OF POINT CLOUD DATA POINTS, EACH COMPRISING A VOLTAGE AND SPATIAL COORDINATES DEFINING A LOCATION ASSOCIATED WITH A HEART, AT WHICH THE VOLTAGE WAS RECORDED, WHEREIN THE PLURALITY OF POINT CLOUD DATA POINTS DEFINES A SHAPE IN A SPACE 102

↓

CONSTRUCT AN OUTER MESH DEFINING AN ENVELOPE FOR OUTERMOST BOUNDARY POINTS OF THE SHAPE 104

↓

CONSTRUCT AN INNER MESH DEFINING AN ENVELOPE FOR INNER BOUNDARY POINTS OF THE SHAPE 106

↓

SELECT POINTS OF THE INNER MESH TO DEFINE ANCHOR POINTS 108

↓

DEFORM POINTS OF THE OUTER MESH USING THE ANCHOR POINTS TO CONTROL THE DEFORMATION 110

METHOD AND SYSTEM TO ASSESS WHETHER ELECTRICAL RECORDINGS DURING CARDIAC MAPPING LIE ON THE MYOCARDIAL SURFACE

FIELD

Embodiments of the present invention relate to cardiac mapping. In particular, embodiments of the present invention relate to point acquisition during cardiac mapping.

BACKGROUND

During cardiac mapping, mapping points are acquired from various locations within the heart. It is desirable that these mapping points are located on the endocardial surface of the heart. However, during mapping, both points within the intracardiac space and points on the endocardial surface are acquired. The acquired points in sum define a point cloud and surface reconstruction techniques are utilized to define the cardiac surface based on the point cloud. Said surface reconstruction techniques comprises interpolation, smoothing, filtering, etc. Ultimately, the goal is to reject points from the point cloud that are not on the endocardial surface.

BRIEF SUMMARY

In one aspect, a method for generating a cardiac map, includes during cardiac mapping in which a mapping catheter is inserted into a heart, receiving a plurality of recordings from the mapping catheter, each recording includes a voltage, and the spatial coordinates of a recording site within the heart indicative of an electrode position of the mapping catheter at the time of acquisition of said voltage, constructing a three-dimensional surface of the heart based on the spatial coordinates of each recording site, performing surface analysis to determine off-surface points in the plurality of recordings where each off-surface point corresponds to a recording from the plurality of recordings which does not lie on the three-dimensional surface, and selectively moving at least some of the off-surface points to the three-dimensional surface based on a predefined threshold.

In another aspect, a method for real-time cardiac mapping, includes while electrical recordings are being made by a mapping catheter, each at a recording location within a heart: processing position information for each recording location to construct a three-dimensional surface that approximates the heart, processing the electrical recordings includes determining which of the recordings are off-surface points defined as being recorded at a recording location that is not on the three-dimensional surface, and for each off-surface point selectively transforming said off-surface point to an on-surface point so that it corresponds to a spatial location that is on the three-dimensional surface.

Other aspects of the invention will be apparent from the detailed description below.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

The phrases "in one embodiment", "in various embodiments", "in some embodiments", and the like are used repeatedly. Such phrases do not necessarily refer to the same embodiment. The terms "comprising", "having", and "including" are synonymous, unless the context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to or combined, without limiting the scope to the embodiments disclosed herein.

Broadly, embodiments of the present invention disclose a technique to perform real-time surface construction for a heart based on point cloud data acquired during a cardiac mapping procedure.

Although not required, the inventive technique is described in the general context of computer-program instructions being executed by a computing device 1100 (which is described later would reference to FIG. 7) which forms part of a cardiac mapping system 1200 (which is described later with respect to FIG. 8).

Program instructions generally include routines, programs, objects, components, data structures, etc., that perform particular tasks or implement particular abstract data types to implement the aforementioned techniques. While the systems and methods are described in the foregoing context, acts and operations described herein after may also be implemented in hardware.

Figure 1:
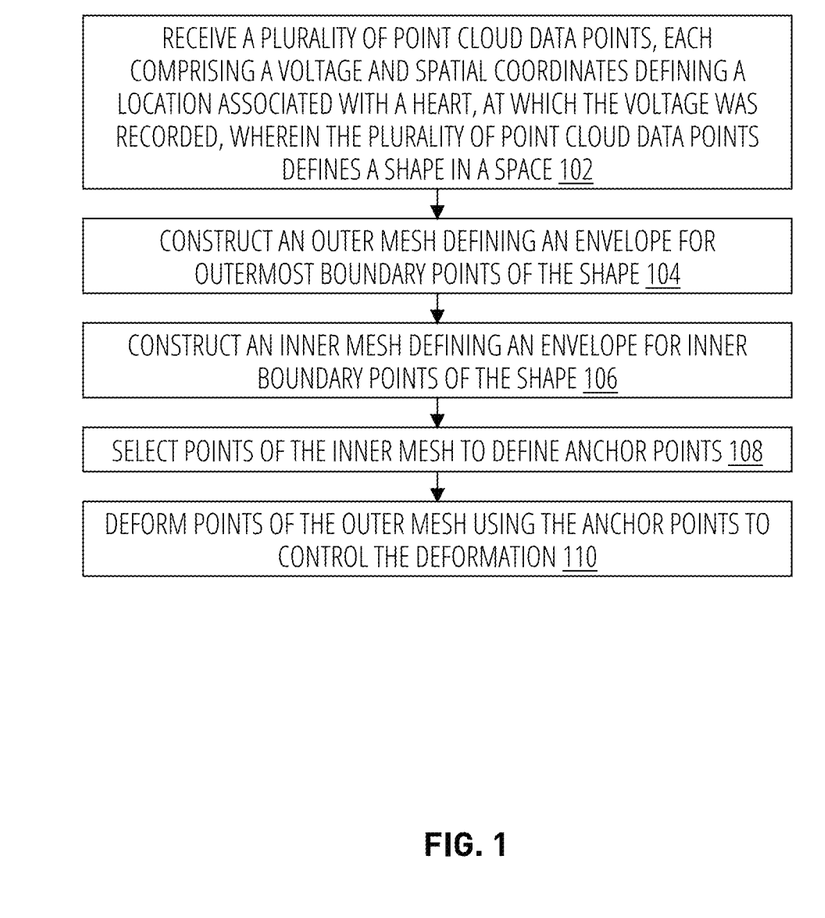
FIG. 1 illustrates a first embodiment of the technique for generating a surface mesh to represent a endocardial surface, in accordance with one embodiment of the invention.
Figure 3:
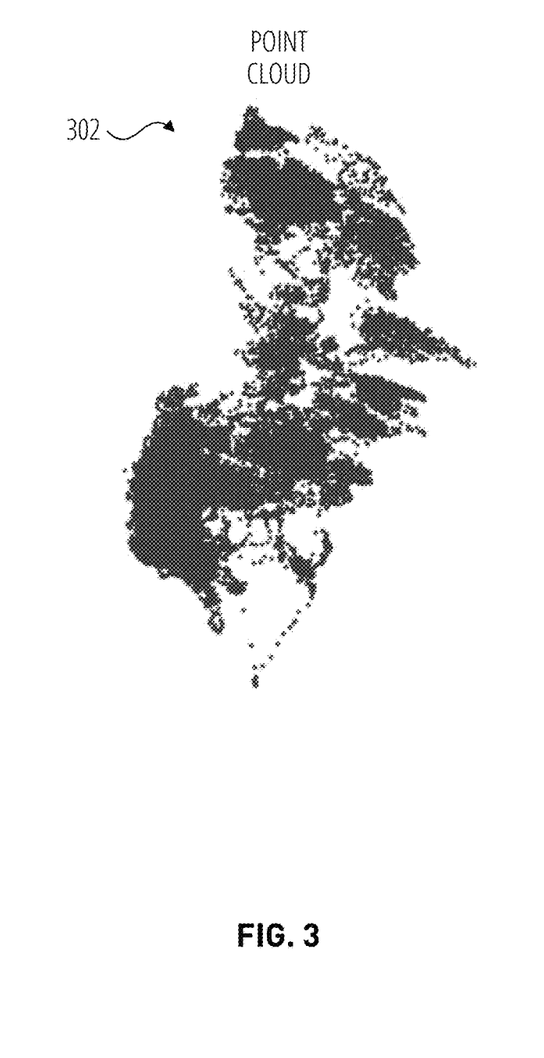
FIG. 3 illustrates a point cloud generated through acquisition of mapping points during cardiac mapping.

FIG. 1 illustrates a first embodiment of the technique. Referring to FIG. 1, at block 202 computing device 1200 receives a plurality of point cloud data points. These points may be acquired in real-time from a mapping catheter, or they may be data points previously acquired and stored in memory. Each point cloud data point comprising a voltage and spatial coordinates defining a location within the heart at which the voltage was recorded. For illustrative purposes, FIG. 3 shows a point cloud 302 comprising a large number of data points. Because the points are closely spaced, some of the regions in the point cloud appear to be continuous surfaces that are completely shaded rather than discrete points. It is to be kept in mind that this artifact is due to the resolution at which the point cloud 302 is displayed. Thus, zooming into the point cloud would show the discrete nature of the points within the cloud. As will be seen, the point cloud 302 define a distinct shape in a space.

Due to cardiac/respiratory motion some of the data points in the cloud may be duplicated. Thus, in one embodiment of the invention, these duplicated points are filtered or removed.

Figure 4:
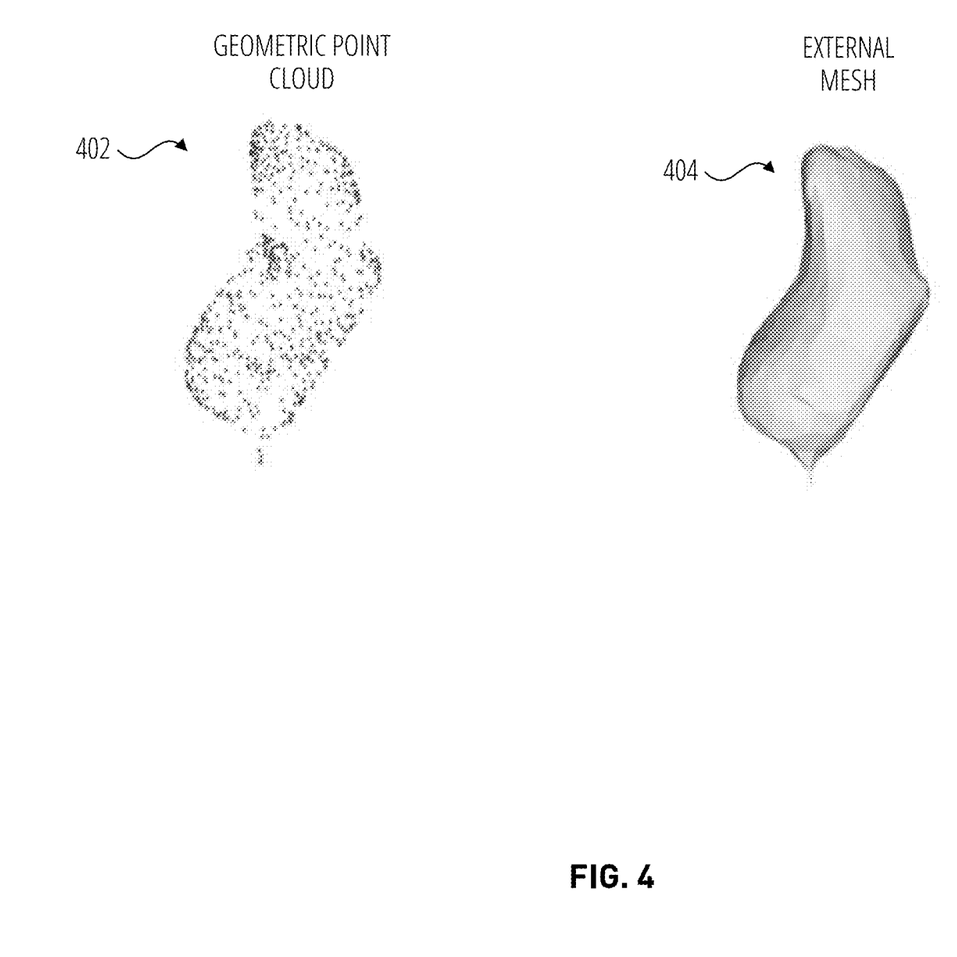
FIG. 4 illustrates generation of an external mesh, in accordance with one embodiment of the invention.

Next at block 104, a surface is constructed from the outermost points in the point cloud 302. This step is illustrated in FIG. 4 of the drawings where reference numeral 402 indicates a geometric point cloud comprising a selection of the outermost points in the point cloud 302. For construction of the surface, an outer mesh that defines an envelope for the outermost boundary points of the shape that defines the point cloud 302 is constructed using techniques known in the field of computational geometry. For example, a convex hull algorithm may be used to generate the outer mesh, in one embodiment. The outer mesh is indicated by reference numeral 404 in FIG. 4. Since the outermost boundary points are used in the mesh construction, the mesh 404 is as a convex or high alpha shape that bulges outwardly like an egg and is lacking in any interior detail of the endocardial surface. Thus, the outer mesh 404 is a crude approximation of the endocardial surface and requires the addition of more features to better approximate the endocardial surface. Advantageously, in one embodiment of the invention a boundary surface is defined and a deformation technique is utilized to deform points on the outer mesh to provide a resultant mesh with better feature definition with the boundary mesh serving as a constraint on the deformation process as will be explained.

Figure 5:
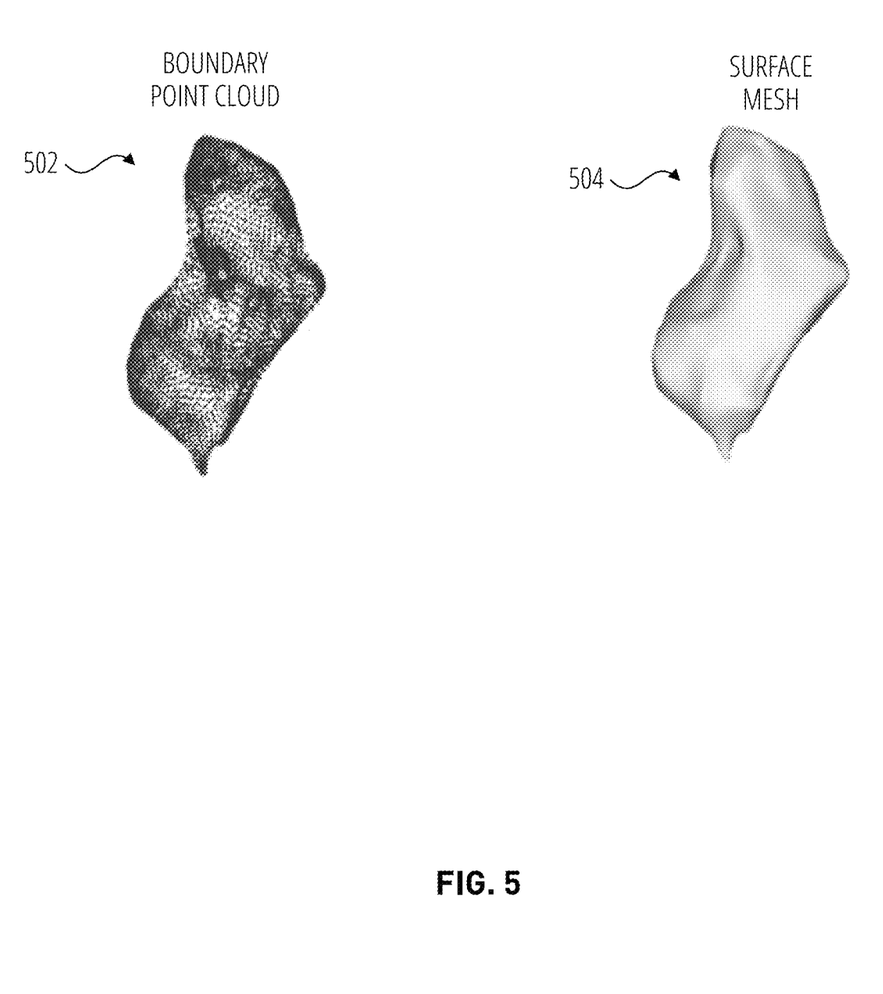
FIG. 5 illustrates generation of the final surface mesh based on the external mesh and a boundary point cloud through a process of Laplace editing, in accordance with one embodiment of the invention.

To define the boundary surface, in one embodiment an inner mesh is constructed using the point cloud 302 as input. The inner mesh defines an envelope for the inner boundary points of the shape of the point cloud data 302. In one embodiment, an alpha hull algorithm is used to generate the boundary surface. The alpha hull algorithm may be configured to include points from the point cloud 302 that are within a certain threshold of the boundary. In one embodiment the threshold is set to be between 1 to 2 mm. FIG. 5 of the drawings illustrates a boundary point cloud 502 produced by the alpha hull algorithm, in accordance with one embodiment.

Next at block 108, points of the inner mesh 502 are selected to define anchor points. Functionally, the anchor points are used to control the deformation process, as will be explained. In some embodiments, all points of the inner mesh may be used as anchor points.

At block 110, the deformation process is executed wherein points of the outer/mesh 404 are deformed using the anchor points to control the deformation. In one embodiment, the deformation may be achieved using the Laplacian editing wherein points of the external mesh 404 are deformed towards the anchor points. The result is a surface mesh 504.

Figure 2:
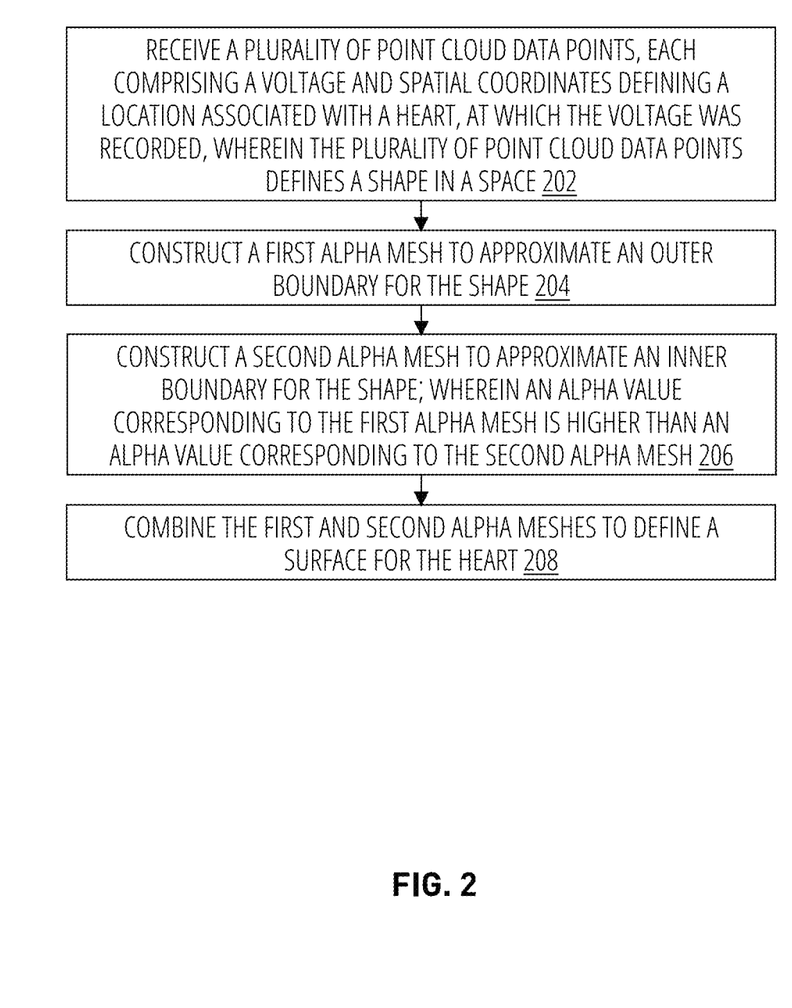
FIG. 2 illustrates a second embodiment of the technique for generating a surplus mesh to represent the endocardial surface, in accordance with one embodiment of the invention.

FIG. 2 illustrates a second embodiment of the technique. Referring to FIG. 2, at block 202, point cloud data points corresponding to a point cloud are received. This block is similar to the block 102 described above. Next, at block 204 a first alpha mesh is constructed to approximate the outer boundary for the shape of the point cloud. At block 206, a second alpha mesh is constructed to approximate the inner boundary for the shape of the point cloud. The alpha value for the first alpha mesh is higher than an alpha value for the second alpha mesh. Thus, the first alpha mesh represents a convex surface similar to the external mesh 404, whereas the second alpha mesh represents a surface similar to the boundary point cloud 502. Both alpha meshes may be constructed using raw point cloud data as input. For construction of the second alpha mesh, a threshold may be used, as described above Finally at block 208, the first and second alpha meshes are combined in order to produce a surface mesh for the heart. In one embodiment, the technique by which the meshes are combined comprises Laplacian editing performed on the first alpha mesh using the second alpha mesh as a constraint on the editing.

Advantageously, embodiments of the present invention also disclosed a technique to assess whether electrical recordings acquired during cardiac mapping lie on the endocardial surface. For ease of reference, the statement will be referred to herein as a "geometric contact assessment".

Figure 6:
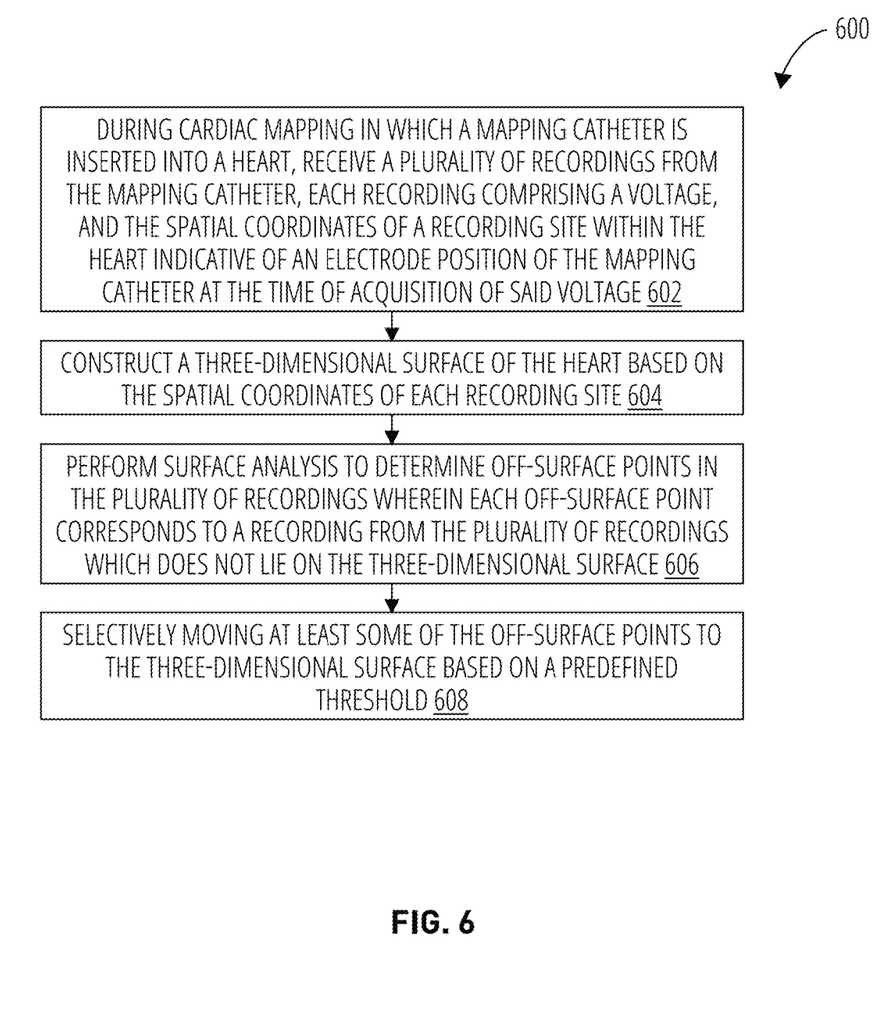
FIG. 6 illustrates a routine 600 in accordance with one embodiment.

Aspects of geometric contact assessment illustrated in FIGS. 6 to 10. FIG. 6 of the drawings illustrates a routine 600 for geometric contract assessment in accordance with one embodiment. In block 602, routine 600 during cardiac mapping in which a mapping catheter is inserted into a heart, receives a plurality of recordings from the mapping catheter, each recording comprising a voltage, and the spatial coordinates of a recording site within the heart indicative of an electrode position of the mapping catheter at the time of acquisition of the voltage. In block 604, routine 600 constructs a three-dimensional surface of the heart based on the spatial coordinates of each recording site. In block 606, routine 600 performs surface analysis to determine off-surface points in the plurality of recordings wherein each off-surface point corresponds to a recording from the plurality of recordings which does not lie on the three-dimensional surface. In block 608, routine 600 selectively moving at least some of the off-surface points to the three-dimensional surface based on a predefined threshold.

It will be noted that block 602 and block 604 relate to construction of the surface mesh for the endocardial surface. In one embodiment these blocks may implement the above-described techniques for surface mesh construction.

Figure 8:
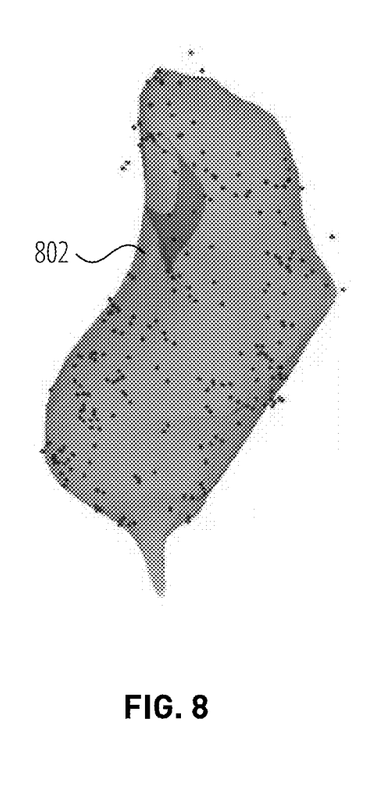
FIG. 8 illustrates an aspect of the subject matter in accordance with one embodiment.

To illustrate surface analysis according to block 606, attention is now drawn to FIG. 8 of the drawings. In this figure, reference 802 indicates the surface mesh constructed to approximate the endocardial surface, in accordance with the techniques disclosed above, whereas the blue dots indicate the location of the recordings made by a mapping catheter. As noted above, each recording comprises a voltage, and spatial coordinates of the recording site in the heart where the recording was made. As will be noted, some of these recordings are located on the surface mesh 802, whereas other points are off the surface. For surface analysis, off-surface points within a defined threshold distance from the surface mesh 802 are considered to be within an acceptable error tolerance. Thus, in accordance with one embodiment, surface analysis involves calculating a distance between each off-surface point and the surface mesh 802 to determine if said off-surface point is within the threshold distance. In one embodiment, the threshold distance may be selected to be between 1 to 2 mm.

Figure 9:
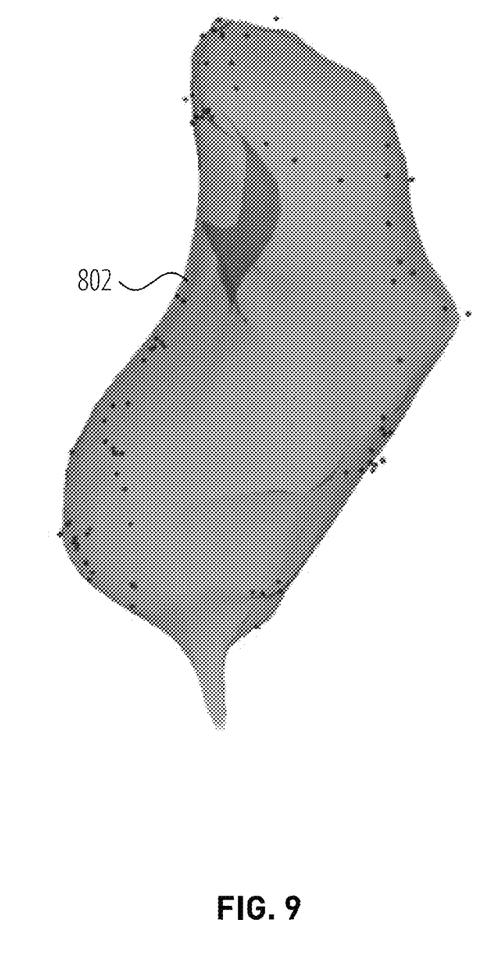
FIG. 9 illustrates an aspect of the subject matter in accordance with one embodiment.
Figure 10:
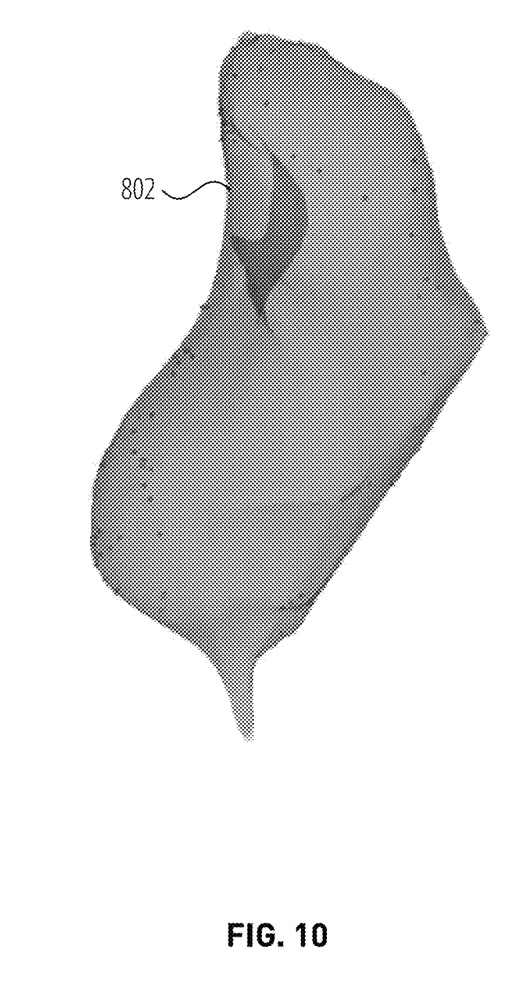
FIG. 10 illustrates an aspect of the subject matter in accordance with one embodiment.

In block 608, only the off-surface points that are within the threshold distance to the surface mesh 802 are selected and moved to the surface mesh. Referring to FIG. 9, the surface mesh 802 is shown again as in FIG. 8. However, it will be noted that there are fewer recordings (gray dots) due to filtering of the recordings that lie outside the threshold. Thus, the recordings shown in FIG. 9 the present only the selected recordings that lie within the threshold distance to the surface mesh 802. When these recordings are moved to the surface, the situation is as shown in FIG. 10 of the drawings, where the surface mesh 802 can be seen with are off-surface points within the threshold moved or projected onto the mesh 802. In this drawing, the points are indicated with gray dots.

Figure 7:
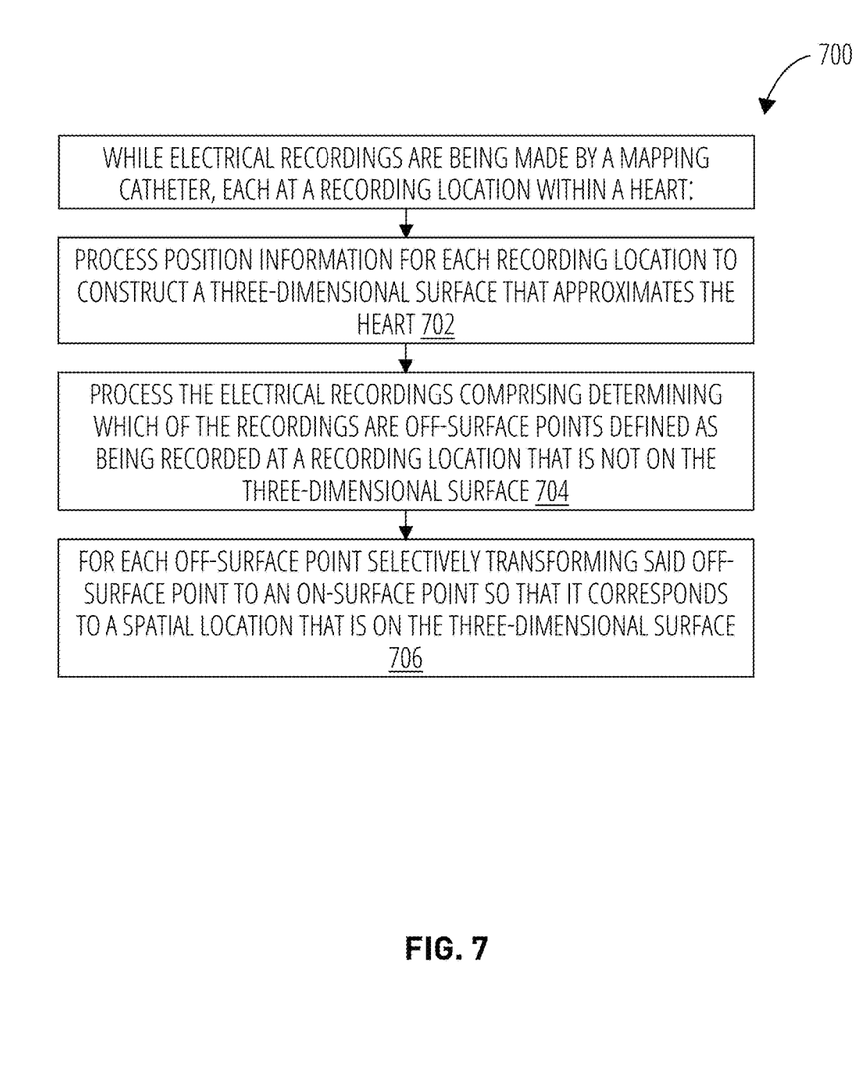
FIG. 7 illustrates a routine 700 in accordance with one embodiment.

FIG. 7 of the drawings illustrates a routine 700 for geometric contract assessment in accordance with another embodiment. In one embodiment, the routine 700 may be performed while electrical recordings are being made by the mapping catheter at each recording location within the heart. In block 702, routine 700 processes position information for each recording location to construct a three-dimensional surface that approximates the heart. In block 704, routine 700 processes the electrical recordings comprising determining which of the recordings are off-surface points defined as being recorded at a recording location that is not on the three-dimensional surface. In block 706, for each off-surface point, routine 700 selectively transforms the off-surface point to an on-surface point so that it corresponds to a spatial location that is on the three-dimensional surface.

Within the routine 700, block 702 includes the above-described techniques to construct a surface mesh. As incoming electrical recordings are received, they are processed as the block 704 to determine if they are on the three-dimensional surface are not. In block 706 only those off surface points that are within the predefined threshold are selectively moved to the three-dimensional surface. Thus, the routine 700 is very similar to the routine 600.

Although not required, the inventive techniques are described in the general context of computer-program instructions being executed by a computing device. Program instructions generally include routines, programs, objects, components, data structures, etc., that perform the particular tasks or implement particular abstract data types. While the systems and methods are described in the foregoing context, acts and operations described herein after may also be implemented in hardware.

Figure 11:
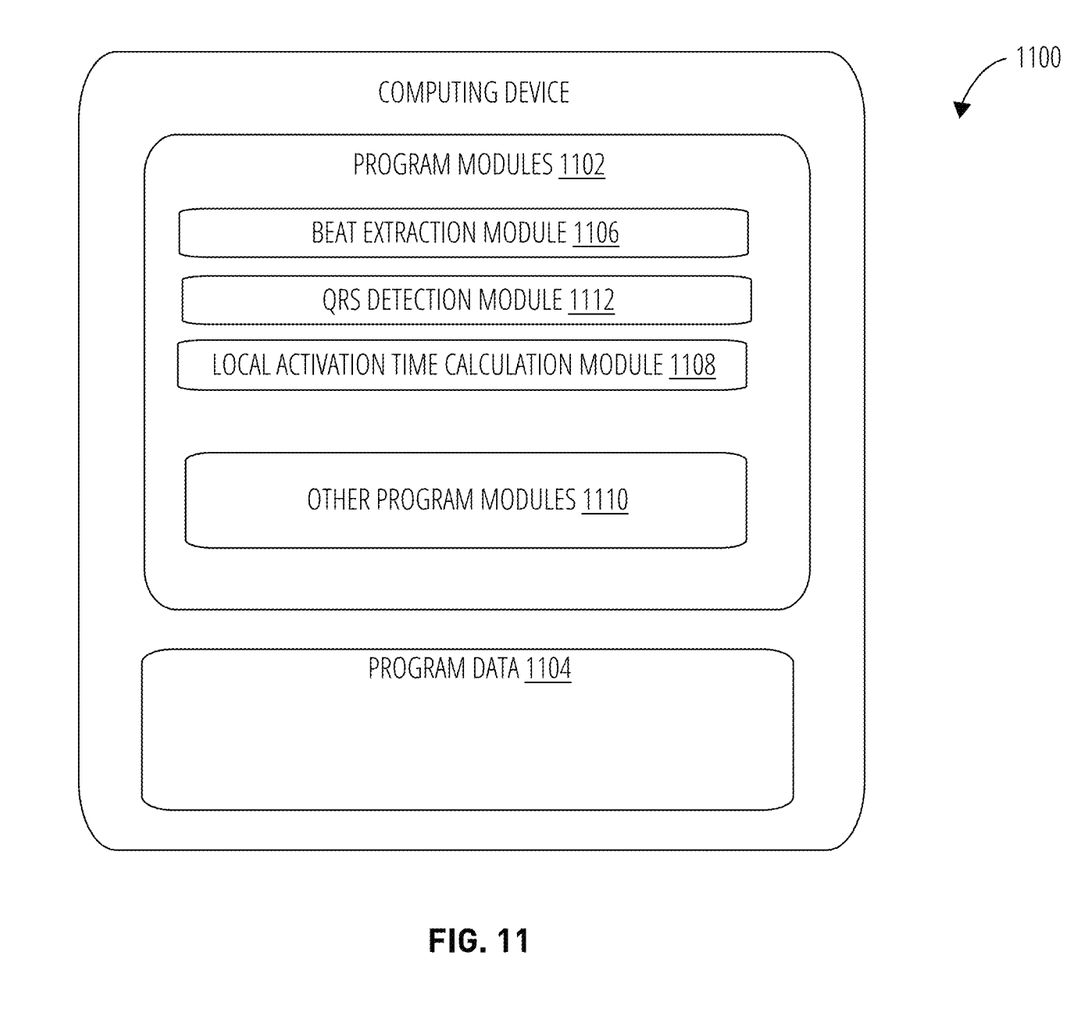
FIG. 11 illustrates one embodiment of high-level block diagram of a computing device for practicing aspects of the invention.

FIG. 11 shows an exemplary system in the form of a computing device 1100 for implementing the techniques disclosed herein, in accordance with one embodiment of the invention. Computing device 1100 may represent any type of computing device such as a laptop, server, etc. Computing device 1100 comprises program modules 1102 and program data 1104. Program modules 1102 may comprise, for example, beat extraction module 1106, local activation time calculation module 1108 and other program modules 1110 such as an operating system, etc.

In use, computing device 1100 may form part of a cardiac mapping system 1200 (which is described later with reference to FIG. 12) configured to receive electrocardiogram (ECG) signals and electrophysiological data for a heart. Cardiac mapping system 1200 is operable to first select a set of surface electrodes which are then driven with current pulses. While the current pulses are being delivered, electrical activity, such as the voltage is measured with at least one of the remaining surface electrodes and in vivo electrodes and stored.

Figure 12:
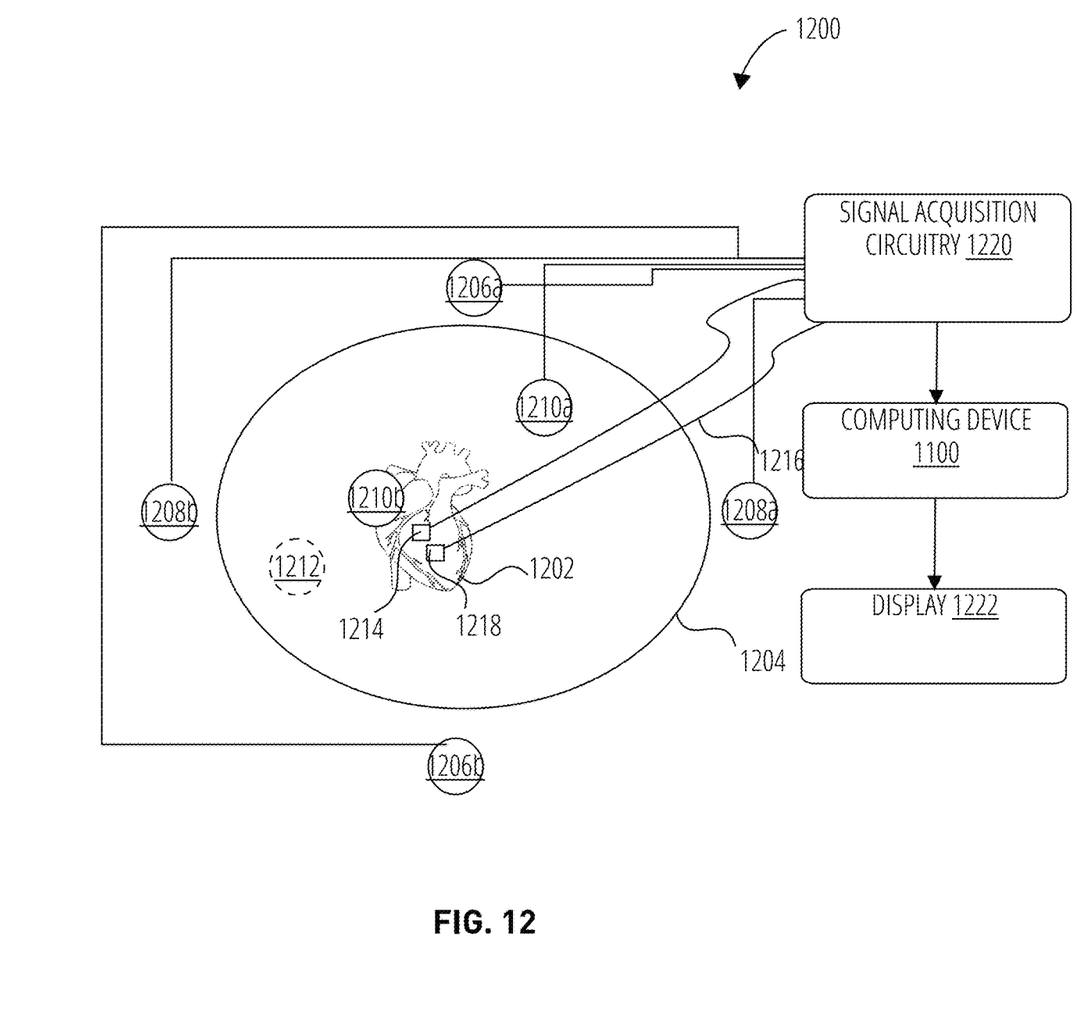
FIG. 12 illustrates an embodiment of a mapping system which may be used to implement aspects of the techniques disclosed herein.

In accordance with one embodiment of the invention, cardiac mapping system 1200 also includes an electrocardiogram system (not shown) to generate electrocardiograms (ECGs) for a patient. The system 1200 also generates electrophysiological (EP) data in the form of EP data points each comprising a recording location within the heart (specified in terms of X, Y, and Z coordinates) and a voltage reading recorded at said location. Thus, each voltage measurement may be associated with position data comprising the spatial location within the heart at which the voltage measurement was made.

FIG. 12, which shows a schematic diagram of a cardiac mapping system 1200 for conducting cardiac electrophysiology studies by navigating a cardiac catheter and measuring electrical activity occurring in a heart 1202 of a patient 1204 and three-dimensionally mapping the electrical activity and/or information related to or representative of the electrical activity. Cardiac mapping system 1200 can be used to help create an anatomical model using one or more electrodes. Cardiac mapping system 1200 can also be used to measure electrophysiology data at a plurality of points along a cardiac surface and store the measured data in association with location information for each measurement point at which the electrophysiology data was measured.

The cardiac mapping system 1200 comprises a computing device 1100, X-axis surface electrodes 706a, 706b, Y-axis surface electrodes 708a, 708b, Z-axis surface electrodes 710a, 710b, surface reference electrode 1212, fixed intra-cardiac electrode 1214, mapping catheter 1216, mapping electrode 1218, signal acquisition circuitry 1220, and a display 1222.

The surface electrodes (e.g., patch electrodes) are shown applied to a surface of patient 1204 along an X-axis, a Y-axis, and a Z-axis. Surface reference electrode 1212 provides a reference and/or ground electrode for the cardiac mapping system 1200. Surface reference electrode 1212 may be an alternative to fixed intra-cardiac electrode 1214. It should also be appreciated that, in addition, the patient 1204 will have most or all of the conventional electrocardiogram (ECG) system leads in place. This ECG information is available to cardiac mapping system 1200 although not illustrated in the FIG. 12.

In one embodiment, the localization/mapping system is the EnSite NavX™ navigation and visualization system of St. Jude Medical, Atrial Fibrillation Division, Inc. Other localization systems, however, may be used in connection with the present invention, including for example, the CARTO navigational and location system of Biosense Webster, Inc. and the LOCALISA intracardiac navigation system of Medtronic, Inc. The localization and mapping systems described in the following patents (all of which are hereby incorporated by reference in their entireties) can be used with the present invention: U.S. Pat. Nos. 6,990,370; 6,978,168; 6,947,785; 6,939,309; 6,728,562; 6,640,119; and 5,983,126.

Each surface electrode is coupled to the multiplex switch of signal acquisition circuitry 1220 and the pairs of electrodes are selected by software running on computing device 1100, which couples the electrodes to a signal generator of the signal acquisition circuitry 1220. Computing device 1100, for example, may comprise a conventional general-purpose computer, a special-purpose computer, a distributed computer, or any other type of computer. The computing device 1100 may comprise one or more processors, such as a single central-processing unit, or a plurality of processing units, commonly referred to as a parallel processing environment.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across a fixed intra-cardiac electrode 1214 resulting from a predetermined set of drive (source-sink) configurations are combined algebraically to yield the same effective potential as would be obtained by simply driving a uniform current along the orthogonal axes.

Any two of the surface electrodes may be selected as a dipole source and drain with respect to a ground reference, e.g., the surface reference electrode 1212 while the unexcited electrodes measure voltage with respect to the ground reference. The mapping/measurement electrode 1218 placed in the heart 1202 is exposed to the field from a current pulse and is measured with respect to ground, e.g., the surface reference electrode 1212. In practice the catheters within the heart may contain multiple electrodes and each electrode potential may be measured. As previously noted, at least one electrode may be fixed to the interior surface of the heart to form a fixed intra-cardiac electrode 1214, which is also measured with respect to ground. Data sets from each of the surface electrodes, the internal electrodes, and the virtual electrodes may all be used to determine the location of the measurement electrode 1218 or other electrodes within the heart 1202.

In summary, the cardiac mapping system 1200 first selects a set of surface electrodes and then drives them with current pulses. While the current pulses are being delivered, electrical activity, such as the voltages measured at least one of the remaining surface electrodes and in vivo electrodes are measured and stored. At this point, compensation for artifacts, such as respiration and/or impedance shifting may be performed as indicated above. As described above, various location data points are collected by the cardiac mapping system 1200 that are associated with multiple electrode locations (e.g., endocardial electrode locations). Each point in the set has coordinates in space.

Figure 13:
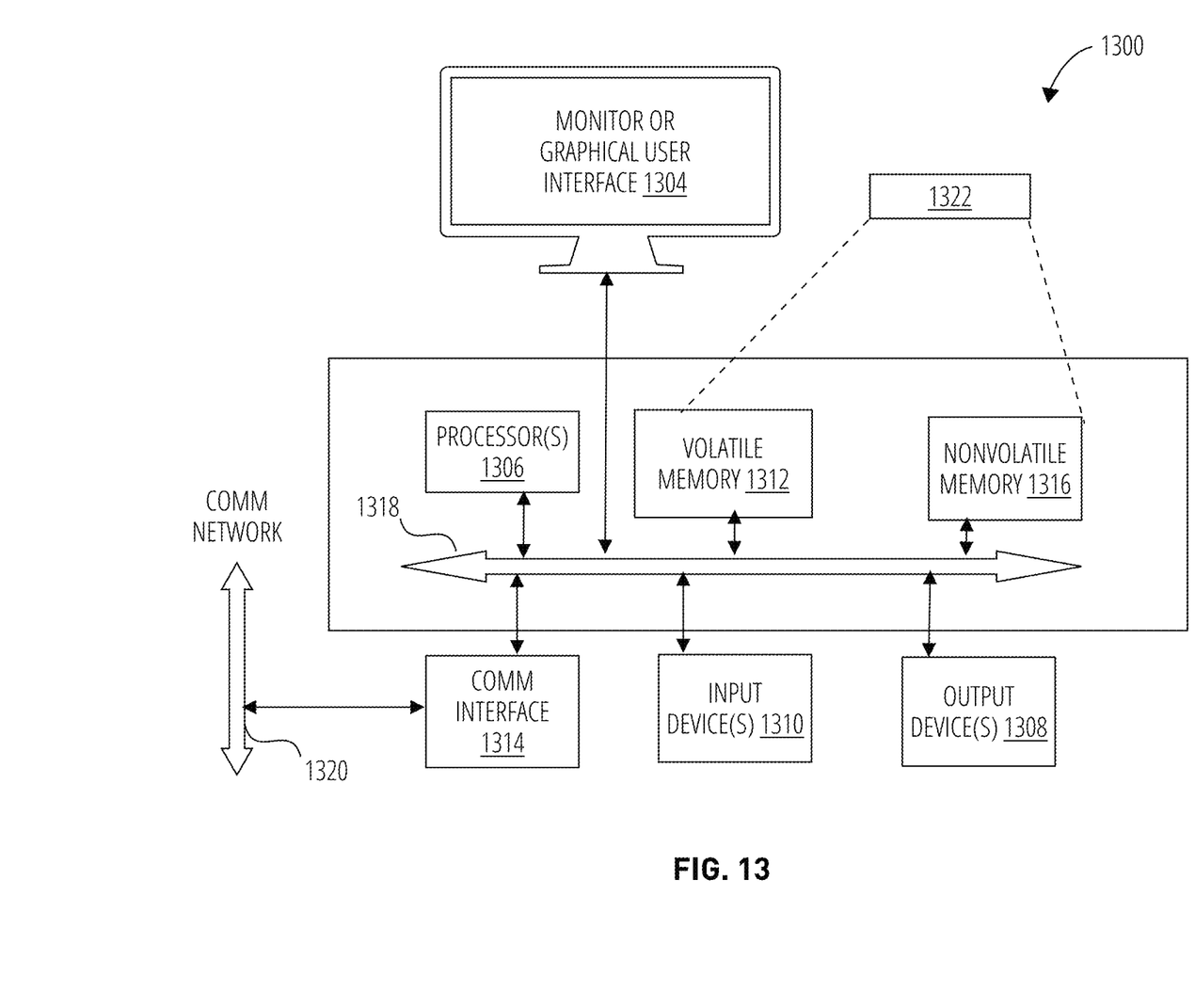
FIG. 13 illustrates a high-level block diagram of exemplary hardware for the computing device 1100.

FIG. 13 is an example block diagram of hardware for the computing device 1100 in accordance with one embodiment of the present invention. FIG. 13 is merely illustrative of a machine system to carry out aspects of the technical processes described herein, and does not limit the scope of the claims. One of ordinary skill in the art would recognize other variations, modifications, and alternatives. In one embodiment, the computing device 1100 typically includes a monitor or graphical user interface 1304, a data processing system 1302, a communication network interface 1314, input device(s) 1310, output device(s) 1308, and the like.

As depicted in FIG. 13, the data processing system 1302 may include one or more processor(s) 1306 that communicate with a number of peripheral devices via a 1318 These peripheral devices may include input device(s) 1310, output device(s) 1308, communication network interface 1314, and a storage subsystem, such as a volatile memory 1312 and a nonvolatile memory 1316.

The volatile memory 1312 and/or the nonvolatile memory 1316 may store computer-executable instructions and thus forming logic 1322 that when applied to and executed by the processor(s) 1306 implement embodiments of the processes disclosed herein.

The input device(s) 1310 include devices and mechanisms for inputting information to the data processing system 1302. These may include a keyboard, a keypad, a touch screen incorporated into the monitor or graphical user interface 1304, audio input devices such as voice recognition systems, microphones, and other types of input devices. In various embodiments, the input device(s) 1310 may be embodied as a computer mouse, a trackball, a track pad, a joystick, wireless remote, drawing tablet, voice command system, eye tracking system, and the like. The input device(s) 1310 typically allow a user to select objects, icons, control areas, text and the like that appear on the monitor or graphical user interface 1304 via a command such as a click of a button or the like.

The output device(s) 1308 include devices and mechanisms for outputting information from the data processing system 1302. These may include the monitor or graphical user interface 1304, speakers, printers, infrared LEDs, and so on as well understood in the art.

The communication network interface 1314 provides an interface to communication networks (e.g., communication network 1320) and devices external to the data processing system 1302. The communication network interface 1314 may serve as an interface for receiving data from and transmitting data to other systems. Embodiments of the communication network interface 1314 may include an Ethernet interface, a modem (telephone, satellite, cable, ISDN), (asynchronous) digital subscriber line (DSL), FireWire, USB, a wireless communication interface such as BlueTooth or WiFi, a near field communication wireless interface, a cellular interface, and the like.

The communication network interface 1314 may be coupled to the communication network 1320 via an antenna, a cable, or the like. In some embodiments, the communication network interface 1314 may be physically integrated on a circuit board of the data processing system 1302, or in some cases may be implemented in software or firmware, such as "soft modems", or the like.

The computing device 1300 may include logic that enables communications over a network using protocols such as HTTP, TCP/IP, RTP/RTSP, IPX, UDP and the like.

The volatile memory 1312 and the nonvolatile memory 1316 are examples of tangible media configured to store computer readable data and instructions to implement various embodiments of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 1312 and the nonvolatile memory 1316 may be configured to store the basic programming and data constructs that provide the functionality of the disclosed processes and other embodiments thereof that fall within the scope of the present invention.

Logic 1322 that implements embodiments of the present invention may be stored in the volatile memory 1312 and/or the nonvolatile memory 1316. Said logic 1322 may be read from the volatile memory 1312 and/or nonvolatile memory 1316 and executed by the processor(s) 1306. The volatile memory 1312 and the nonvolatile memory 1316 may also provide a repository for storing data used by the logic 1322.

The volatile memory 1312 and the nonvolatile memory 1316 may include a number of memories including a main random access memory (RAM) for storage of instructions and data during program execution and a read only memory (ROM) in which read-only non-transitory instructions are stored. The volatile memory 1312 and the nonvolatile memory 1316 may include a file storage subsystem providing persistent (non-volatile) storage for program and data files. The volatile memory 1312 and the nonvolatile memory 1316 may include removable storage systems, such as removable flash memory.

The bus subsystem 1318 provides a mechanism for enabling the various components and subsystems of data processing system 1302 communicate with each other as intended. Although the communication network interface 1314 is depicted schematically as a single bus, some embodiments of the bus subsystem 1318 may utilize multiple distinct busses.

It will be readily apparent to one of ordinary skill in the art that the computing device 1300 may be a device such as a smartphone, a desktop computer, a laptop computer, a rack-mounted computer system, a computer server, or a tablet computer device. As commonly known in the art, the computing device 1300 may be implemented as a collection of multiple networked computing devices. Further, the computing device 1300 will typically include operating system logic (not illustrated) the types and nature of which are well known in the art.

Terms used herein should be accorded their ordinary meaning in the relevant arts, or the meaning indicated by their use in context, but if an express definition is provided, that meaning controls.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

What is claimed is:

1. A method, for generating a cardiac map, comprising:
during cardiac mapping in which a mapping catheter is inserted into a heart, receiving a plurality of recordings from the mapping catheter, each recording comprising a voltage, and spatial coordinates of a recording site within the heart indicative of an electrode position of the mapping catheter at a time of acquisition of said voltage;
constructing a three-dimensional surface of the heart based on the spatial coordinates of each recording site, wherein the three-dimensional surface of the heart comprises an outer mesh surface and an inner mesh surface wherein the outer mesh surface is calculated using a first algorithm and the inner mesh surface is calculated using a second algorithm;
performing surface analysis of the constructed three-dimensional surface to determine off-surface points in the plurality of recordings wherein each off-surface point corresponds to a recording from the plurality of recordings which does not lie on the three-dimensional surface; and
selectively moving at least some of the off-surface points to the three-dimensional surface based on a predefined threshold.

2. The method of claim 1, wherein the selective moving comprises moving a recording to the three-dimensional surface, when it is determined that a distance between the recording site associated with the recording and the three-dimensional surface is below the predefined threshold.

3. The method of claim 2, wherein moving the recording to the three-dimensional surface comprises migrating said recording spatially to a point on the three-dimensional surface that is determined to be closest to said recording.

4. A method for real-time cardiac mapping, comprising:
while electrical recordings are being made by a mapping catheter, each at a recording location within a heart:
processing position information for each recording location to construct a three-dimensional surface that approximates the heart wherein the three-dimensional surface of the heart comprises an outer mesh surface and an inner mesh surface wherein the outer mesh surface is calculated using a first algorithm and the inner mesh surface is calculated using a second algorithm;

processing the electrical recordings comprising determining which of the recordings are off-surface points defined as being recorded at a recording location that is not on the constructed three-dimensional surface; and for each off-surface point selectively transforming said off-surface point to an on-surface point so that it corresponds to a spatial location that is on the three-dimensional surface.

5. The method of claim 4, wherein the off-surface point is transformed to an on-surface point when its recording location is within a predefined threshold distance to the three-dimensional surface.

6. The method of claim 4, wherein the selective transformation is performed periodically.

7. The method of claim 6, wherein the selective transformation is performed prior to completion of the construction of the three-dimensional surface.

8. A computing apparatus comprising:

a processor; and a memory storing instructions that, when executed by the processor, configure the apparatus to:

during cardiac mapping in which a mapping catheter is inserted into a heart, receiving a plurality of recordings from the mapping catheter, each recording comprising a voltage, and spatial coordinates of a recording site within the heart indicative of an electrode position of the mapping catheter at a time of acquisition of said voltage;

construct a three-dimensional surface of the heart based on the spatial coordinates of each recording site, wherein the three-dimensional surface of the heart comprises an outer mesh surface and an inner mesh surface wherein the outer mesh surface is calculated using a first algorithm and the inner mesh surface is calculated using a second algorithm;

perform surface analysis of the constructed three-dimensional surface to determine off-surface points in the plurality of recordings wherein each off-surface point corresponds to a recording from the plurality of recordings which does not lie on the three-dimensional surface; and selectively move at least some of the off-surface points to the three-dimensional surface based on a predefined threshold.

9. The computing apparatus of claim 8, wherein the selective moving comprises moving a recording to the three-dimensional surface, when it is determined that a distance between the recording site associated with the recording and the three-dimensional surface is below the predefined threshold.

10. The computing apparatus of claim 9, wherein moving the recording to the three-dimensional surface comprises migrate said recording spatially to a point on the three-dimensional surface that is determined to be closest to said recording.

11. A computing apparatus comprising:

a processor; and a memory storing instructions that, when executed by the processor, configure the apparatus to:

while electrical recordings are being made by a mapping catheter, each at a recording location within a heart:

process position information for each recording location to construct a three-dimensional surface that approximates the heart, wherein the three-dimensional surface of the heart comprises an outer mesh surface and an inner mesh surface wherein the outer mesh surface is calculated using a first algorithm and the inner mesh surface is calculated using a second algorithm;

process the electrical recordings comprising determining which of the recordings are off-surface points defined as being recorded at a recording location that is not on the constructed three-dimensional surface; and for each off-surface point selectively transform said off-surface point to an on-surface point so that it corresponds to a spatial location that is on the three-dimensional surface.

12. The computing apparatus of claim 11, wherein the off-surface point is transformed to an on-surface point if when its recording location is within a predefined threshold distance to the three-dimensional surface.

13. The computing apparatus of claim 11, wherein the selective transformation is performed periodically.

\* \* \* \* \*